(12) United States Patent
Omura et al.

(10) Patent No.: US 6,251,379 B1
(45) Date of Patent: Jun. 26, 2001

(54) HAIR COSMETIC COMPOSITION

(75) Inventors: Takayuki Omura; Tomiyuki Nanba, both of Kanagawa (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/513,689

(22) Filed: Feb. 25, 2000

(30) Foreign Application Priority Data

Feb. 26, 1999 (JP) .................................................. 11-51770

(51) Int. Cl.$^7$ ................................ A61K 7/06; A61K 7/11; A61K 7/00

(52) U.S. Cl. .................. 424/70.1; 424/70.11; 424/70.12; 424/70.122; 424/70.14; 424/401

(58) Field of Search ..................................... 424/401, 70.1, 424/70.11, 70.12, 70.122, 70.14

(56) References Cited

U.S. PATENT DOCUMENTS 6,066,316 * 5/2000 Shiojima et al. .................. 424/70.19
6,190,647 * 2/2001 Karlen et al. ........................ 424/70.2
6,190,648 * 2/2001 Kouzu et al. ........................ 424/70.6

FOREIGN PATENT DOCUMENTS

10077208 * 3/1998 (JP) .
10077210 * 3/1998 (JP) .

* cited by examiner

Primary Examiner—Shelley A. Dodson
Assistant Examiner—Marina Lamm
(74) Attorney, Agent, or Firm—Townsend & Banta

(57) ABSTRACT

The present invention provides a hair-cosmetic composition containing the following ingredients (A) and (B): (A): keratose which is cationized with a quaternary ammonium salt, and (B): a silicone derivative. The hair cosmetic composition imparts excellent gloss and smooth feel to damaged hair, while bonding and mending split ends of hair fibers.

7 Claims, No Drawings

HAIR COSMETIC COMPOSITION

BACKGROUND OF THE INVENTION

1. Field of the Invention

The present invention relates to hair cosmetic compositions.

2. Related Art

Roughly speaking, the hair has two functions; a "protective function" and an "esthetic function." The "protective function" of the hair literally refers to the function of protecting the body, protecting the head from sunlight, heat, and cold, and exerting a buffering function against impact applied from the outside. The "esthetic function" of the hair refers to the function of the hair through which people can project an impression of themselves. It is commonly accepted that the impression of a person may be greatly changed if color, style, or another characteristic of the person's hair is changed.

The hair, fulfilling such important functions, perpetually undergoes a variety of stresses from the outside. That is, the hair is subjected to not only natural stresses such as ultraviolet rays from the sun and dirt but also even more stringent stresses such as shampooing, brushing, heat from a drier, and beauty treatments such as hair-dyeing and bleaching. As a result, well-known problems of the hair are caused, including dry and rough hair, increased number of split ends, broken hair, falling hair, and reduced strength of hair fibers.

Therefore, in order to prevent or mitigate the above-described damage to the hair, various attempts have been proposed from different approaches.

One such attempt is use of an oily ingredient, such as silicone oil, high-molecular-weight dimethylpolysiloxane, high-molecular-weight methylphenylpolysiloxane, ester oil, or hydrocarbon oil, for the purpose of imparting gloss and smoothness to the hair. In particular, silicone oils have recently been used very often, as they have low surface tension, exhibit excellent compatibility with the hair, and provide beautiful gloss.

However, silicone oils encounter limitations when used as oily ingredients of a hair cosmetic composition. For example, use of silicone oil in a large amount or for a prolonged period makes hair greasy.

Cationic surfactants are also frequently used for imparting smoothness to hair fibers. However, the gloss imparted thereby is not fully satisfactory, and besides, incorporation of cationic surfactants in large amounts is unfavorable in terms of safety.

Japanese patent application laid-open (kokai) Nos. 183517/1988, 24301/1988, 313712/1988, and 85918/1993 disclose techniques for prevention of damage to the hair while imparting gloss and smoothness thereto. According to those publications, this objective is achieved by either incorporation, into a hair cosmetic composition, of high-molecular-weight dimethylpolysiloxane, high-molecular-weight methylphenylpolysiloxane, or amino-modified or ammonium-modified high-molecular-weight silicone, or combined use of a certain species of a polysiloxane-oxyalkylene copolymer and a silicone derivative. However, these techniques are not fully satisfactory in terms of their split-end-mending effect and gloss-imparting effect.

Accordingly, there still remains need for development of a hair cosmetic composition which provides excellent gloss and smooth feel to damaged hair while bonding and mending split ends of hair fibers.

A current mainstream trend in the development of hair cosmetic compositions is to solve the above problems by incorporation of ingredients which are derived from naturally occurring substances.

Indeed, with an aim toward protecting and mending hair fibers, there are provided hair cosmetic compositions which contain, as a base ingredient, a material prepared from a naturally-occurring substance. Examples of the material include proteins, polysaccharides, extracts, natural polymers, and monomers and oligomers (e.g., amino acids and peptides) that constitute any of these materials.

As a candidate ingredient derived from a naturally-occurring substance which is to be incorporated into a hair cosmetic composition, the present inventors have focused on "keratin." Keratin is a hard protein and is present in great amounts in hair fibers. The amino acid composition of keratin greatly differs from that of collagen, silk, or any other animal-derived hard protein. Therefore, the present inventors have contemplated that incorporation of a component derived from keratin would be preferable for use with hair, particularly in consideration of compatibility of the component with hair fibers.

When the keratin-derived ingredient is incorporated into a hair cosmetic composition, intrinsic properties of keratin are preferably maintained as intact as possible. In addition, an easy-to-handle form of the keratin-derived ingredient that permits practical use is preferably chosen.

SUMMARY OF THE INVENTION

In view of the foregoing, the objects of the present invention are to select a keratin-derived ingredient that satisfies the above conditions, and to provide a hair cosmetic composition that imparts excellent gloss and smooth feel to damaged hair, while bonding and mending split ends of hair fibers, by use of such a keratin-derived ingredient.

The present inventors have conducted earnest studies toward solving the above objects, and have found when keratin hydrolysate "keratose" is cationized with a quaternary ammonium salt, and such cationized keratose is chosen as the keratin-derived ingredient and incorporated into a hair cosmetic composition in combination with a silicone derivative (in particular, high-molecular-weight silicone or amino-modified or ammonium-modified high-molecular-weight silicone), the composition can retain moisture of damaged hair and exhibit excellent split-hair mending effect and gloss-imparting effect, thus leading to completion of the invention.

Accordingly, the present invention provides a hair-cosmetic composition containing the following ingredients (A) and (B):

(A): keratose which is cationized with a quaternary ammonium salt, and (B): a silicone derivative.

The above and various other objects, features and many of the attendant advantages of the present invention will become better understood by reference to the following detailed description of the preferred embodiments.

DETAILED DESCRIPTION OF PREFERRED EMBODIMENTS

The present invention will next be described in detail.

As described above, the hair cosmetic composition of the present invention contains (A) keratose cationized with a quaternary ammonium salt and (E) a silicone derivative, to thereby exhibit effects on hair damage.

Essential Ingredients (A) and (B) which are Incorporated into the Hair Cosmetic Composition of the Present Invention 1. An essential ingredient which is incorporated into the hair cosmetic composition of the present invention (ingredient (A)), i.e., "keratose cationized with quaternary ammonium salt" is a keratose derivative which is obtained by cationization of keratose, which is a hydrolysate of keratin, by use of a quaternary ammonium salt.

Keratose serving as a basic material of ingredient (A) can be produced by hydrolysis of keratin under relatively mild conditions (see Japanese patent application laid-open (kokai) Nos. 77210/1998 and 77208/1998).

Keratin which is to be hydrolyzed for producing keratose is so-called "true keratin." No particular limitation is imposed on the type of a raw material of the keratin, and examples of the raw material include hair, wool, feathers, animal horns, egg membranes, and hoofs.

The average molecular weight of keratose produced by hydrolysis of keratin is preferably 5,500–35,200, in consideration of the following: The original structure of keratin should be maintained to the extent possible in keratose, keratose can recover damaged hair and impart moistness or smoothness to hair, and keratose should be of practical use as an ingredient incorporated into a hair cosmetic composition, i.e., production of the composition is easy. When the average molecular weight of keratose is less than 5,500, characteristics of keratin as a protein constituting the hair tend to be lost, which is unsatisfactory. In contrast, when the average molecular weight is in excess of 35,200, such keratose may not be of practical use, such that production of a composition containing such keratose may be difficult.

The average molecular weight of keratose is calculated on the basis of the number of amino acid residues which constitute keratose. Namely, the average molecular weight is calculated on the basis of supposition that the molecular weight of an amino acid residue is 110 (see "New Biochemistry by Lehninger" authored by Jiro Koyama et al., published by Hirokawa Shoten, First Volume, pp. 141–142 (1988)), and thus keratose containing 50–320 amino acid residues is preferable. (In consideration of the number of amino acids which constitute the keratose, it is presumed that this keratose is derived from keratin in such a manner that the keratin molecule is cut at two to eight points along its length.) Therefore, the above-described range of average molecular weight is a standard, and keratose having an average molecular weight which falls outside the range may be employed in the hair cosmetic composition of the present invention.

Keratose having a relatively high average molecular weight as described above can be obtained by hydrolysis of keratin under mild conditions. When keratin is hydrolyzed by a mildly reactive compound such as performic acid, peracetic acid, or hydrogen peroxide, the following three types of keratose can be extracted from the hydrolyzate: α-keratose, which dissolves in alkaline water but does not dissolve in acidic water; β-keratose, which dissolves in neither alkaline water nor acidic water; and γ-keratose, which dissolves in both alkaline water and acidic water. Specifically, desired keratose can be obtained through, for example, the following procedures.

Firstly, keratin is hydrolyzed by use of 2–5% performic acid, peracetic acid, or hydrogen peroxide at a temperature within a range of room temperature to 100° C. for 30 minutes to three hours, and washed with water. Subsequently, the thus-obtained hydrolysate is dissolved in an alkali aqueous solution such as an aqueous solution of sodium hydroxide or aqueous ammonia.

Secondly, β-keratose, which does not dissolve in an alkali aqueous solution, is filtered by use of a filtration cloth, and the remaining solution is acidified by use of an acid such as sulfuric acid or hydrochloric acid to thereby adjust the pH of the solution to around 4. Subsequently, a milky precipitate generated during acidification and a transparent supernatant are separated by filtration.

Thirdly, the milky precipitate is re-dissolved in an alkali solution, and the solution is dialyzed with a cellophane tube for dialysis, a dialysis membrane, an ultrafiltration (UF) membrane, or a reverse osmotic (RO) membrane, to thereby obtain α-keratose. The supernatant is subjected to dialysis treatment in the same manner as the above solution, and spray-dried or freeze-dried, to thereby obtain water-soluble γ-keratose.

Thus, keratose having an average molecular weight which falls within the above range can be obtained. of the three types of keratose, α-keratose or γ-keratose is preferably chosen, for the following reasons: in practice, keratose serving as a starting material of a keratose derivative employed in the present invention should be soluble in a conventionally used solvent in order to produce a composition.

Keratose which is obtained by hydrolysis of keratin under mild conditions, particularly α-keratose or γ-keratose, is cationized with a quaternary ammonium salt, to thereby obtain a desired cationized keratose.

The cationized keratose is a keratose derivative which is produced by cationization of keratose, specifically by addition of a quaternary ammonium salt to a terminal amino group, a terminal carboxyl group, a side-chain amino group of a lysine residue, a side-chain imidazole group of a histidine residue, and/or a side-chain phenolic hydroxyl group of a tyrosine residue, which residues constitute keratose. (Hereinafter these groups will be referred to as "reactive residues.")

A cationization agent for cationizing keratose by addition of a quaternary ammonium salt to the aforementioned groups of keratose, which is used in the present invention, is a quaternary ammonium compound represented by the following formula (1):

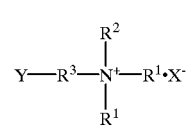

(1)

wherein each of two $R^1$, which may be the same or different each other, represents a lower alkyl group; $R^2$ represents a $C_1$–$C_{20}$ alkyl group or a $C_2$–$C_{20}$ alkenyl group; $R^3$ represents a $C_1$–$C_{24}$ alkylene group or a hydroxyalkylene group; X represents a halogen atom; Y represents a reactive group; and $R^3$ and Y may be linked to each other to form a glycidyl group.

In formula (1), a lower alkyl group R may be methyl, ethyl, or propyl. When $R^3$ represents a $C_1$–$C_{20}$ alkyl group, the alkyl group may be a linear or a branched alkyl group. Such an alkyl group may be methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, isopropyl, isobutyl, sec-butyl, tert-butyl, neopentyl, tert-pentyl, or ischexyl, but is not limited thereto. Of these, propyl or butyl is preferable, and n-propyl or n-butyl is particularly preferable.

When $R^2$ represents a $C_2$–$C_{20}$ alkenyl group, $R^2$ may be 1-propenyl, 2-butenyl, 1,3-butadienyl, 2-pentenyl, 3-hexenyl, 5-heptenyl, 9-decenyl, 2-tridecenyl, 2-methyl-2-butenyl, 9-octadecenyl, or 9,12-octadecadienyl, but is not limited thereto. Of these, 1-propenyl or 2-butenyl is preferable.

A halogen atom X may be fluorine, chlorine, bromine, or iodine. Of these, chlorine is preferable.

When $R^3$ represents a $C_1$–$C_{24}$ alkylene group, $R^3$ may be methylene, ethylene, trimethylene, tetramethylene, pentamethylene, hexamethylene, or octamethylene.

When $R^3$ represents a $C_1$–$C_{24}$ hydroxyalkylene group, $R^3$ may be hydroxyalkylene in which one or more hydroxy groups are bonded to each of the aforementioned $C_1C_{24}$ alkylene groups. Examples of such hydroxyalkylene groups include hydroxypropyl, hydroxybutyl, hydroxyhexyl, hydroxyoctyl, hydroxydecyl, hydroxydodecyl, hydroxytetradecyl, and hydroxyhexadecyl.

No particular limitation is imposed on the type of a reactive group Y, so long as the group Y reacts with the above-described reactive residue of keratose to thereby successfully add a quaternary ammonium compound (1) to the reactive residue. Specific examples of the reactive group Y include a halogen atom, such as fluorine, chlorine, bromine, or iodine. Meanwhile, as described above, the reactive group Y may form a glycidyl group, together with $R^3$.

Examples of such quaternary ammonium compounds (1) include 3-chloro-2-hydroxypropyloctadecyldimethylammonium chloride, glycidyloctadecyldimethylammonium chloride, 3-chloro-2-hydroxypropylheptadecyldimethylammonium chloride, glycidylheptadecyldimethylammonium chloride, 3-chloro-2-hydroxypropylhexadecyldimethylammonium chloride, glycidylhexadecyldimethylammonium chloride, 3-chloro-2-hydroxypropylpentadecyldimethylammonium chloride, glycidylpentadecyldimethylammonium chloride, 3-chloro-2-hydroxypropyltetradecyldimethylammonium chloride, glycidyltetradecyldimethylammonium chloride, 3-chloro-2-hydroxypropyltridecyldimethylarmonium chloride, glycidyltridecyldimethylammonium chloride, 3-chloro-2-hydroxypropyldodecyldimethylammonium chloride, glycidyldodecyldimethylammonium chloride, 3-chloro-2-hydroxypropylcocoalkyldimethylamonium chloride, glycidylcocoalkyldimethylammonium chloride, 3-chloro-2-hydroxypropylundecyldimethylamonium chloride, glycidylundecyldimethylammonium chloride, 3-chloro-2-hydroxypropyldecyldimethylammonium chloride, glycidyldecyldimethylammonium chloride, 3-chloro-2-hydroxypropylnonyldimethylammonium chloride, glycidylnonyldimethylammonium chloride, 3-chloro-2-hydroxvpropyloctyldimethylammonium chloride, glycidyloctyldimethylammonium chloride, 3-chloro-2-hydroxypropylheptyldimethylammonium chloride, glycidylheptyldimethylanmonium chloride, 3-chloro-2-hydroxypropylhexyldimethylammonium chloride, glycidylhexyldimethylammonium chloride, 3-chloro-2-hydroxypropylpentyldimethylammonium chloride, glycidylpentyldimethylammonium chloride, 3-chloro-2-hydroxropylbutyldimethylamonium chloride, glycidylbutyldimethylammonium chloride, 3-chloro-2-hydroxypropylpropyldimethylammonium chloride, glycidylpropyldimethylammonium chloride, 3-chloro-2-hydroxypropylethyldimethylammonium chloride, glycidylethyldimethylanmoniun chloride, 3-chloro-2-hydroxypropyltrimethylammonium chloride, glvcidyltrimethylammonium chloride; 3-chloro-2-hydroxypropyloctadecyldiethylammonium chloride, glycidyloctadecyldiethylammonium chloride, 3-chloro-2-hydroxypropylheptadecyldiethylammonium chloride, glycidylheptadecyldiethylammonium chloride, 3-chloro-2-hydroxypropylhexadecyldiethylammonium chloride, glycidylhexadecyldiethylammoniun chloride, 3-chloro-2-hydroxypropylpentadecyldiethylammonium chloride, glycidylpentadecyldiethylammonium chloride, 3-chloro-2-hydroxypropyltetradecyldiethylammonium chloride, glycidyltetradecyldiethylammonium chloride, 3-chloro-2-hydroxypropyltridecyldiethylammonium chloride, glycidyleridecyldiethylammonium chloride, 3-chloro-2-hydroxypropyldodecyldiethylammonium chloride, glycidyldodecyldiethylammonium chloride, 3-chloro-2-hydroxypropylcocoalkyldiethylammon;ium chloride, glycidylcocoalkyldiethylammonium chloride, 3-chloro-2-hydroxypropylundecyldiethylammonium chloride, glycidylundecyldiethylanmonium chloride, 3-chlorc-2-hydroxypropyldecyldiethylammonium chloride, glycidyldecyldiethylammonium chloride, 3-chloro-2-hydroxvpropylnonyldiethylammonium chloride, glycidylnonyldiethylammonium chloride, 3-chloro-2-hydroxypropyloctyldiethylammonium chloride, glycidyloctyldiethylammonium chloride, 3-chloro-2-hydroxypropylheptyldiethylammonium chloride, glycidylheptyldiethylammonium chloride, 3-chloro-2-hydroxypropylhexyldiethylammonium chloride, glycidylhexyldiethylammonium chloride, 3-chloro-2-hydroxypropylpentyldiethylammonium chloride, glycidylpentyldiethylammonium chloride, 3-chloro-2-hydroxypropylbutyldiethylammonium chloride, glycidylbutyldiethylammonium chloride, 3-chloro-2-hydroxypropylpropyldiethylammonium chloride, glycidylpropyldiethylammonium chloride, and 3-chloro-2-hydroxypropyltriethylammonium chloride. The quaternary ammonium compound (1) which may be used is not limited thereto.

Generally, when the number of carbon atoms of $R^2$ increases, the $R^2$ tends to have high hydrophobicity and low solubility in water, whereas when the number of carbon atoms decreases, the $R^2$ tends to have high hydrophilicity and low solubility in alcohol. When the number of carbon atoms of $R^2$ is very high or very low, cationization of keratose does not proceed efficiently.

Cationization of keratose, particularly α-keratose or γ-keratose, by use of the above-described quaternary ammonium compound (1) can be carried out through, for example, the following procedures.

Firstly, α-keratose is dissolved in an alkali aqueous solution of pH 7–12, in an amount of approximately 1–10 wt. % on the basis of the entirety of the solution. Alternatively, γ-keratose is dissolved in the solution, in an amount of approximately 1–20 wt. % on the basis of the entirety of the solution. The resultant solution is maintained at a temperature within a range of room temperature to 80° C., preferably a range of 40–70° C.

Secondly, a quaternary ammonium compound (1) is added to the resultant reaction solution, in an amount of approximately 5–15 wt. % on the basis of the entirety of the reaction solution, preferably approximately 10 wt. %. The mixture is stirred for 8–48 hours, preferably 18–36 hours, with occasional adjustment of pH so as to prevent lowering thereof.

Thirdly, the reaction mixture is acidified (approximately pH 3–4) to thereby terminate cationization of keratose.

After termination of reaction, preferably, non-reacted substances are removed from the reaction mixture by means of any of a variety of methods, to thereby obtain a cationized keratose derivative which is suitable as an ingredient incorporated into the hair cosmetic composition of the present invention. For example, a lower alcohol is added to the reaction mixture so that the final alcohol concentration is 40–80 vol. %, preferably 50–70 vol. %, and a precipitate generated in the mixture is removed through centrifugation or filtration by use of a membrane filter, to thereby obtain a transparent aqueous alcoholic solution- The thus-obtained aqueous alcoholic solution is dialyzed with any dialysis means such as a cellophane tube for dialysis, a ° F. membrane, or an RO membrane, and the dialyzed solution can be (1) formed into a powder by spray-drying or freeze-drying; (2) concentrated in the form of liquid; or (3) formed into a powder and re-dissolved in water or alcoholic water to form a solution. In the case of (3) above, when α-keratose is employed, a milky dispersion is obtained, whereas γ-keratose is employed, a transparent aqueous solution is obtained.

Thus-obtained keratose derivative cationized with a quaternary ammonium compound is incorporated into the hair cosmetic composition of the present invention, and the amount of the derivative incorporated into the composition may be appropriately chosen in consideration of a specific product form of the composition and combination between the derivative and other ingredients. No particular limitation is imposed on the amount of the derivative, but preferably, the derivative is incorporated into the composition in an amount of 0.01–5.0 wt. % on the basis of the entirety of the composition, more preferably 0.1–2.0 wt. %. When the amount is less than 0.01 wt. %, the composition tends to exhibit insufficient effects in preventing hair damage, whereas the composition tend to have stickiness when the amount is in excess of 5.0 wt. %, which is unsatisfactory.

2. The other essential ingredient which is incorporated into the hair cosmetic composition of the present invention (ingredient (B)) is a silicone derivative. Examples of the silicone derivative include (1) dimethyl silicone oils such as octamethyltrisiloxane, decamethyltetrasiloxane, methylsiloxane, and highly-polymerized methylpolysiloxane; (2) cyclic silicone oils such as octamethylcyclotetrasiloxane and dodecamethylcyclohexasiloxane; (3) methylphenyl silicone oils such as methylphenylpolysiloxane; (4) polyether-modified silicone oils such as polyoxyethylene-methylpolysiloxane copolymer, poly(oxyethylene-oxyoropylene)-methylpolvsiloxane copolymer, decamethylcyclopentasiloxane, octamethylcyclotetrasiloxane, and laurylmethiconecopolyol; (5) trimethylsiloxysilicate; (6) amodimethicone emulsions such as aminoethylaminopropylsiloxane-dimethylsiloxane copolymer emulsion; (7) dimethyl silicone emulsion; (8) crosslinked methylpolysiloxane; (9) silicone compounds such as silicone resin; (10) stearoxy-modified silicone such as stearoxmethylpolysiloxane; (11) alkyl-modified silicone; (12) amino-modified silicone; (13) carboxyl-modified silicone; (14) higher-fatty-acid-modified silicone; (15) epoxy-modified silicone; (16) vinyl-group-containirig silicone; (17) alcohol-modified silicone; (18) polyether-modified silicone; (19) alkyl-polyether-modified silicone;

(20) fluorine-modified silicone; (21) aminopolyether-modified silicone; (22) eugenol-modified silicone; and (23) dimethyl silicone emulsion.

Of these derivatives, particularly, a silicone derivative represented by the following formulas are preferably employed.

High-molecular-weight silicone which is a silicone derivative represented by formula (I):

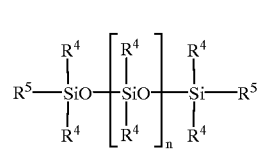

(I)

wherein $R^4$ represents a methyl group or a phenyl group (not all $R^4$ represents a phenyl group), $R^5$ represents a methyl group or a hydroxyl group, and n represents an integer of 3,000–20,000; and amino-modified or ammonium-modified high-molecular-weight silicone which is a silicone derivative represented by formula (II):

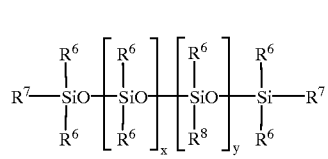

(II)

wherein $R^6$ represents a methyl group or a phenyl group (not all $R^6$ represents a phenyl group), $R^7$ represents a methyl group, a hydroxyl group, or the same group as $R^{8,}$ $R^6$ represents a substituent having an amino group or an ammonium group, which substituent is represented by formula $R^9Z$ ($R^9$ represents a $C_3$–$C_6$ alkylene group and Z represents a monovalent group selected from the group consisting of —$N(R^{10})_2$, —$N^+(R^{10})_3A^-$, —$N(R^{10})(CH_2)_dN(R^{10})_2$, —$NR^{10}(CH_2)_dN^+(R^{10})_3A^-$, and —$NR^{10}(CH_2)_aN(R^{10})$ C=O($R^{11}$), wherein $R^{10}$ represents a hydrogen atom or a $C_1$–$C_4$ alkyl group, $R^{10}$ represents a $C_1$–$C_4$ alkyl group, A represents chlorine, bromine, or iodine, and d represents an integer of 2–6), and each of x and y represents a positive integer, x+y being 3,000–20,000 and y/x being $\frac{1}{500}$–$\frac{1}{10,000}$.

In silicone derivative (I), which is high-molecular-weight silicone, preferably, $R^4$ and $R^5$ both represent a methyl group. Silicone derivative (I) has a molecular weight of approximately 370,000–1,500,000, and assumes a soft-rubber property at room temperature.

Specific examples of silicone derivative (I) include dimethylpolysiloxane, methylphenylpolysiloxane, dimethylpolysiloxane containing a terminal hydroxvl group, and methylphenylpolysiloxane containing a terminal hydroxyl group. Such silicone derivative (I) is commercially available as, for example, "SE30" and "SE70" (products of General Electric Co.).

In silicone derivative (II), which is amino-modified or ammonium-modified high-molecular-weight silicone, preferably $R^6$ is a methyl group, $R^7$ is a methyl group or a hydroxyl group, and $R^8$ is —$(CH_2)_3NH_2$, —$(CH_2)_3N$ $(CH_3)_2$, or —$(CH_2)_3N^+(CH_3)_3Cl^-$.

As described above, in formula (II), x+y is 3,000–20,000, preferably 4,000–20,000. When x+y is less than 3,000, silicone derivative (II) has an oily property, and thus the derivative tends to exhibit insufficient effects in protecting hair. In contrast, when x+y is in excess of 20,000, the derivative exhibits poor compatibility with silicone oil described below and is not practical in production of a composition. In addition, as described above, y/x is $\frac{1}{500}$–$\frac{1}{10,000}$, preferably $\frac{1}{500}$–$\frac{1}{2,000}$. Wqhen y/x is in excess of $\frac{1}{500}$, high-molecular-weight silicone contains amino or ammonium groups in a large amount, and thus cross-linking reaction may occur during production of silicone derivative (II) and a composition containing such silicon derivative may have an odor of a raw material, which is unsatisfactory. In contrast, when y/x is less than 1/10,000, interaction between amino or ammonium groups and hair is insufficient, and thus desired effects in protecting hair may not be maintained.

Silicone derivative (II), which is amino-modified high-molecular-weight silicone or ammonium-modified high-molecular-weight silicone. can be produced by means of a conventional method. For example, the derivative can be produced by condensation polymerization of γ-aminopropylmethyldiethoxysilane, cyclic dimethylpolysiloxane and hexamethyldisiloxane in the presence of an alkali catalyst, but a method for producing the derivative is not limited thereto. Silicone derivative (II) assumes a soft rubber property. When the hair cosmetic composition of the present invention containing the derivative is used in a large amount, or when the composition is continuously used for a prolonged period of time, the composition does not provide hair and the scalp with stickiness. The composition provides hair with excellent gloss and smooth feel, and has excellent effects in protecting hair.

In the hair cosmetic composition of the present invention, the above-described ingredient (B), i.e., silicone derivatives, may be incorporated singly or in combination of two or more species. Preferably silicone derivatives (I) and (II) are incorporated in combination.

When silicone derivatives (I) and (II) are incorporated into the hair cosmetic composition of the present invention in combination, in order to reduce stickiness and improve sensation during use, the weight ratio of silicone derivative (I) to silicone derivative (II) is preferably 1:9–9:1, more preferably 2:8–8:2.

When the weight ratio of silicone derivative (II) to silicone derivative (I) is very high, stickiness may occur and sensation during use tends to be unfavorable, whereas when the ratio is very low, effects in mending split ends or adhering to hair tend to be insufficient, which is unsatisfactory.

The amount of a silicone derivative serving as ingredient (B) incorporated into the hair cosmetic composition of the present invention may be appropriately chosen in consideration of a specific product form of the composition and combination between the derivative and other ingredients. No particular limitation is imposed on the amount of the derivative; preferably, the derivative is incorporated into the composition in an amount of 0.1–50.0 wt. % on the basis of the entirety of the composition, more preferably 1.0–30.0 wt. %. When the amount is less than 0.1 wt. %, the composition tends to exhibit insufficient effects in preventing hair damage, whereas the derivative is difficult to dissolve in the composition when the amount is in excess of 50.0 wt. %, which is unsatisfactory in practice.

When a silicone derivative serving as ingredient (B), particularly the above-described silicone derivative (I) or (II), is incorporated into the hair cosmetic composition of the present invention, the derivative is dissolved in volatile oil of low boiling point and incorporated into the composition, which is preferable and practical. Depending on the product form, the silicone derivative and volatile oil may be incorporated into the composition independently, and the derivative may be dissolved in the oil in a product.

Examples of volatile oil of low boiling point which may be used in the composition include linear silicone oil, cyclic silicone oil, and isoparaffin-type hydrocarbon oil.

The aforementioned linear silicone oil may be represented by formula (III):

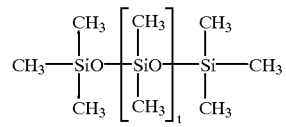

wherein t represents an integer of 0–650.

Examples of such linear silicone oil include dimethylpolysiloxane (viscosity: 0.65–5 mPa•s/25° C.).

The aforementioned cyclic silicone oil may be represented by formula (IV):

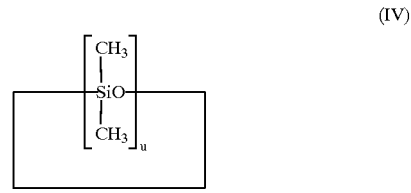

wherein u represents an integer of 3–7.

Examples of such cyclic silicone oil include octamethylcyclotetrasiloxane, decamethylcyclopentasiloxane, and tetradecanethylcyclohexasiloxane.

The aforementioned isoparaffiin-type hydrocarbon oil preferably has a boiling point of 60–260° C. at atmospheric pressure. Examples of such hydrocarbon oil include Isopar A (registered trademark), Isopar C, D, E, G. H, K, L, and M (products of Exxon Corp.); Shellsol 71 (registered trademark, product of Shell); and Soltrol 100 (registered trademark), Soltrol 130 and 220 (products of Phillips), which are commercially available.

Such volatile oils may be incorporated into the hair cosmetic composition of the present invention singly or in combination of two or more species. The weight ratio of the oil to a silicone derivative serving as ingredient (B) is preferably 1–50.

As described above, when (A) keratose cationized with a quaternary ammonium salt and (3) a silicone derivative, serving as essential ingredients, are incorporated into a hair cosmetic composition, there is provided a hair cosmetic composition which can impart excellent gloss and smooth feel to damaged hair and can bond and mend split ends.

Product Form of the Hair Cosmetic Composition of the Present Invention

If necessary, other ingredients which are generally incorporated into a hair cosmetic composition may further be incorporated into the hair cosmetic composition of the present invention so long as they do not impede the effects of the present invention in qualitatively or quantitatively. Examples of such ingredients include oily ingredients such as liquid paraffin, squalane, lanolin derivatives, higher alcohols, ester oils, avocado oil, palm oil, beef tallow, jojoba oil, polyoxyalkylene glycol ether and oligoester of polyoxyalkylene glycol ether and carboxylic acid, and terpene-type hydrocarbons; water-soluble polyalcohols such as ethylene glycol, propylene glycol, 1,3-butylene glycol, glycerin, sorbitol, and polyethylene glycol; humectants sucn as hyaluronic acid, chondroitin sulfate, and pyrrolidonecarboxylate; UV-ray absorbing agents; UV-ray diffusing agents; resins such as acrylic resins and polyvinylpyrrolidone; proteins such as soybean proteins, gelatin, collagen, silk fibroin, and elastin, or protein hydrolyzates; preservatives such as ethylparaben and butylparaben; activating agents such as amino acids, biotin, and pantothenic acid derivatives; antiseborrheic agents such as γ-oryzanol, sodium dextran sulfate, and vitamin E; diluents such as ethanol, isopropanol, and tetrachlorodifluoroethane; thickeners such as carboxyvinyl polymers; drugs; perfumes; and coloring agents.

The hair cosmetic composition of the present invention may be formed into any arbitrary product form; i.e., a solubilization system, an emulsification system, a powder-dispersion system, an oil-water two-phase system, or an oil-water-powder three-phase system.

EXAMPLES

The present invention will next be described in more detail by way of examples, which should not be construed as limiting the invention thereto. Unless otherwise specified, the amount of each ingredient incorporated into a composition is represented by "wt. %" on the basis of the entirety of the composition.

Production Examples

Production Example 1
Production of Cationized α-keratose (1)

Firstly, glacial acetic acid and aqueous hydrogen peroxide (concentration of 35%) were weighed at a weight ratio of 8:2 and homogeneously mixed, to thereby prepare a solution of peracetic acid (100 g). Defatted wool (10 g) was washed thoroughly and placed into the peracetic acid solution, and then stirred at 60° C. for three hours, to thereby hydrolyze wool keratin. The hydrolyzed wool keratin was removed, washed with water, and dissolved in 0.5M aqueous ammonia (maintained at 50° C.) (100 g) under thorough stirring. Insoluble matter was removed from the aqueous ammonia solution by means of a filter cloth, and the pH of the filtrate was adjusted to 4 or less by use of sulfuric acid. After adjustment of the pH, the aqueous ammonia solution containing precipitated milky-white α-keratose derived from keratin was dialyzed and the thus-purified α-keratose was dried by use of a spray-drier, to thereby obtain a powder thereof.

The thus-obtained α-keratose had an average molecular weight of 18,000 as measured through high-nerformance liquid chromatography.

The α-keratose (10 g) which was subjected to no further treatment was dissolved in an aqueous solution of caustic soda (pH 10) (100 g), and the solution was maintained at 65° C. To the solution, glycidyltrimethylammonium chloride (effective ingredient 74%, product of Sakamcto Yakuhin) (10 ml) was added. The resultant mixture was stirred for 18 hours with compensating lowering in pH for an initial one hour. Hydrochloric acid was added to the reaction mixture, to thereby acidify the mixture and terminate the reaction. The reaction-terminated mixture was dialyzed against distilled water by use of a cellophane tube for obtaining a molecular weight fraction of 5000 so as to remove unreacted matter. The resultant insoluble matter was removed by filtration and spray-dried, to thereby obtain a powder at a yield of 80%. The powder was dissolved in water again, to thereby obtain a milky liquid (pH 6.5) in which a quaternary ammonium salt-added α-keratose was dispersed.

Production Example 2
Production of Cationized γ-keratose

Iin a manner similar to that employed in Production Example 1, glacial acetic acid and aqueous hydrogen peroxide (concentration of 35%) were weighed at a weight ratio of 8 2 and homogeneously mixed, to thereby prepare a solution of peracetic acid (100 g). Defatted wool (10 g) was thoroughly washed and placed into the peracetic acid solution, and then stirred at 60° C. for three hours, to thereby hydrolyze wool keratin. The hydrolyzed wool keratin was removed and dissolved in water. The solution was dissolved in 0.5M aqueous ammonia (maintained at 50° C.) (100 g) under thorough stirring. Insoluble matter was removed from the aqueous ammonia solution by means of a filter cloth, and the pH of the filtrate was adjusted to 4 or less by use of sulfuric acid. The solution was centrifuged, to thereby separate a clear supernatant containing γ-keratose. After the separated supernatant was concentrated by means of an evaporator, the solution was dialyzed. The thus-purified γ-keratose was dried by use of a spray-drier, to thereby obtain a powder thereof. The thus-obtained γ-keratose had an average molecular weight of 9,800 as measured through high-performance liquid chromatography.

The γ-keratose (20 g) which was subjected to no further treatment was dissolved in an aqueous solution of caustic soda (pH 10) (100 g), and the solution was maintained at 65° C. To the solution, glycidyltrimethylammonium chloride (effective ingredient 74%, product of Sakamoto Yakuhin) (10 ml) was added. The resultant mixture was stirred for 18 hours with compensating lowering in pH for an initial one hour. Hydrochloric acid was added to the reaction mixture, to thereby acidify the mixture and terminate the reaction. The reaction-terminated mixture was dialyzed against distilled water by use of a cellophane tube for obtaining a molecular weight fraction of 3500 so as to remove unreacted matter. The resultant insoluble matter was removed by filtration and spray-dried, to thereby obtain a powder at a yield of 85%. The powder was dissolved in water again, to thereby obtain a clear liquid (pH 6.5) in which a quaternary ammonium salt-added γ-keratose was dissolved.

Production Example 3
Production of Cationized α-keratose (2)

The α-keratose (10 g) which was obtained in production Example 1 and subjected to no further treatment was dissolved in an aqueous solution of caustic soda (pH 10) (100 g), and the solution was maintained at 65° C. To the solution, glycidyltrimethylammonium chloride (effective ingredient 74%, product of Sakamoto Yakuhin) (10 ml) was added. The resultant mixture was stirred for 18 hours with compensating lowering in pH for an initial one hour, to thereby cause addition reaction. Subsequently, the pH of the reaction mixture was adjusted to 3.5, and ethanol (2.5 times by volume) was added to the resultant mixture such that the final ethanol concentration was approximately 70% The formed precipitate was removed through centrifugation, to thereby obtain a clear aqueous ethanolic solution. The solution was dialyzed against distilled water by use of a cellophane tube for obtaining a molecular weight fraction of 3500. The resultant insoluble matter was removed by filtration and spray-dried, to thereby obtain a powder at a yield of 60%. The powder was dissolved in 50% aqueous ethanol again, to thereby obtain a clear aqueous alcoholic solution (pH 6.5) in which a quaternary ammonium salt-added α-keratose, which was insoluble to water and soluble to an alcohol-water mixture, was dissolved Production Example 4
Untreated α-keratose The α-keratose which was subjected to no further treatment, obtained in Production Example 1 was employed as "untreated α-keratose."

Production Example 5

Untreated γ-keratose

The γ-keratose which was subjected to no further treatment, obtained in Production Example 2 was employed as "untreated γ-keratose."

Confirmation of Degree of Cationization

The amino group contents of quaternary ammonium salt-added α-keratose produced in Production Examples 1 and 3; the amino group content of quaternary ammonium salt-added γ-keratose produced in Production Example 2; and the amino group contents of untreated α-keratose and γ-keratose of Production Examples 4 and 5 were compared with one another, to thereby investigate the degree of addition of a quaternary ammonium compound to amino groups in each keratose.

The state in which all amino groups reacted with a quaternary ammonium compound was evaluated as 100% cationization, while the state in which half the amino groups remained unreacted was evaluated as 50% cationization.

The amino group content was measured on the basis of a TNBS (TriNitro Benzene Sulfonic acid) method (Tadanori Ono et al., "*Chemical Modification of Protein (Part 1)*, published by Gakkai Shuppan Center, p38 (1986)).

Specifically, to a solution (1 ml) of 0.5 wt. % of one of the respective keratose samples in distilled water, a borate-phosphate buffer (pH 8.0) (4 ml) and an aqueous 0.1% TNBS solution (4 ml) were added. The mixture was shielded from light by use of aluminum foil or like material and allowed to react at 40° C. for one hour. Subsequently, a IN HCl (114 ml) and a 10% SDS (4 ml) were added to the reaction mixture, to thereby terminate the reaction. The absorbance of each mixture at 340 nm was measured, and the amino group contents of quaternary ammonium salt-added keratose samples and those of untreated keratose samples were compared. The results are shown in Table 1.

TABLE 1

| Sample | Cationization degree (%) |
| --- | --- |
| Production Ex. 1 (cationized α-keratose) | 85 |
| Production Ex. 2 (cationized γ-keratose) | 95 |
| Production Ex. 3 (cationized α-keratose) | 53 |
| Production Ex. 4 (untreated α-keratose) | 0 |
| Production Ex. 5 (untreated γ-keratose) | 0 |

As is clear from Table 1, each untreated keratose sample (Production Example 4 or 5) had a cationization degree of 0%, whereas keratose samples treated with a quaternary ammonium compound (Production Examples 1 to 3) had certain cationization degrees, which indicate that cationization of amino groups reached a considerable degree.

From the above, it is clear that when keratose is treated with a specific quaternary ammonium compound, cationized keratose is in fact formed.

Examples of formulations according to the hair cosmetic composition of the present invention and a conventional hair cosmetic composition will next be described as Examples and Comparative Examples, where (1) stickiness to the hands, (2) combing force, (3) smoothness, (4) gloss of hair, and (5) effect in mending split ends were evaluated in manners described below.

Example 1

Hair Blow

| Ingredient | Amount ( wt. %) |
| --- | --- |
| (1) decamethylcyclopentasiloxane | 15.0 |
| (2) dimethylpolysiloxane (20 mPa · s) | 3.0 |
| (3) 1,3-butylene glycol | 2.0 |
| (4) polyoxyethylene hydrogenated castor oil (60EO) | 2.0 |
| (5) α-keratose (Production Ex. 3) | 1.0 |
| (6) ethanol | 15.0 |
| (7) deionized water | balance |
| (8) perfume | 0.3 |

Method of Production

Ingredient (2) was added to Ingredient (1), and the mixture was added to a mixture of Ingredients (3) and (4). The resultant mixture was emulsified. Subsequently, the emulsion was mixed with Ingredients (5) to (8), to thereby obtain a hair blow.

Example 2

Hair Mousse

| Ingredient | Amount (wt. %) |
| --- | --- |
| (1) octamethylcyclotetrasiloxane | 10.0 |
| (2) high-molecular-weight silicone [formula (I), wherein each of $R^4$ and $R^5$ represents a methyl group, respectively, and n is 3000] | 2.0 |
| (3) ammonium-modified high-molecular-weight silicone (formula (II), wherein 10% of $R^6$ represents a phenyl group and the remainder of $R^6$ represents a methyl group; $R^7$ represents a methyl group; $R^8$ represents $-(CH_2)_3N^+(CH_3)_3Cl^-$; x is 10,000; and y is 2] | 1.0 |
| (4) propylene glycol | 2.5 |
| (5) polyoxyethylene hydrogenated castor oil (40EO) | 2.0 |
| (6) α-keratose (Production Ex. 1) | 2.5 |
| (7) γ-keratose (Production Ex. 2) | 2.5 |
| (8) ethanol | 8.0 |
| (9) deionized water | balance |
| (10) n-butane | 7.0 |
| (11) perfume | 0.1 |

Method of Production

Ingredients (2) and (3) were dissolved in Ingredient (1), and the mixture was added to a mixture of Ingredients (4) and (5). The resultant mixture was emulsified. Subsequently, the emulsion was mixed with Ingredients (6), (7), (8), (9), and (11), to thereby prepare a solution, which was charged into an aerosol container. The container was equipped with a stopper valve, and filled with Ingredient (10), to thereby obtain a hair mousse.

Example 3

Hair Cream

| Ingredient | Amount (wt. %) |
| --- | --- |
| (1) decamethylcyclohexasiloxane | 25.0 |
| (2) amino-modified high-molecular-weight silicone [formula (II), wherein $R_6$ represents a methyl group; $R^7$ represents a hydroxyl group; $R^8$ | 6.0 |

-continued

| Ingredient | Amount (wt. %) |
|---|---|
| represents -(CH$_2$)$_3$N(CH$_3$)$_2$; x is 3000; and y is 6] | |
| (3) glycerin | 3.0 |
| (4) polyoxyethylene hydrogenated castor oil (120EO) | 3.0 |
| (5) γ-keratose (Production Ex. 2) | 3.0 |
| (6) ethanol | 4.0 |
| (7) deionized water | balance |
| (8) polyvinyl alcohol | 1.0 |
| (9) perfume | 0.15 |

Method of Production

Ingredient (2) was dissolved in Ingredient (1), and the mixture was added to a mixture of Ingredients (3) and (4). The resultant mixture was emulsified. Subsequently, the emulsion was mixed with Ingredients (5) to (9), to thereby obtain a hair cream.

Example 4
Hair Gel

| Ingredient | Amount (wt. %) |
|---|---|
| (1) polyether-modified silicone [Silicone SC1014M, product of Shin-Etsu Chemical Co., Ltd.] | 3.0 |
| (2) carboxyvinyl polymer [Hiviswako 104, product of Wako Pure Chemicals Industries, Ltd.] | 2.0 |
| (3) glycerin | 5.0 |
| (4) vinylpyrrolidone/vinyl acetate copolymer [PVP/VA · S-630, product of ISP] | 3.0 |
| (5) α-keratose (Production Ex. 1) | 5.0 |
| (6) ethanol | 5.0 |
| (7) deionized water | balance |
| (8) sodium hydroxide | 0.5 |
| (9) perfume | 0.5 |

Method of Production

Ingredient (2) was dissolved in Ingredient (7). To the mixture, Ingredients (1), (3), (4), (5), (6), (8), and (9) were successively added, to thereby obtain a hair gel.

Example 5
Conditioning Shampoo

| Ingredient | Amount (wt. %) |
|---|---|
| (1) triethanolamine lauryl polyoxyethylene(3) sulfate (30% aq. solution) | 10.0 |
| (2) sodium lauryl polyoxyethylene(3) sulfate (30% aq. solution) | 20.0 |
| (3) sodium lauryl sulfate (30% aq. solution) | 5.0 |
| (4) lauroyldiethanolamide | 3.0 |
| (5) lauryl dimethylaminoacetic acid betaine (35% aq. solution) | 7.0 |
| (6) dimethylsilicone emulsion | 2.5 |
| (7) cationized γ-keratose (Production Ex. 2) | 0.2 |
| (8) ethylene glycol distearate | 2.0 |
| (9) perfume | 0.3 |
| (10) paraben | 0.1 |
| (11) sequestering agent | 0.1 |
| (12) pH-adjuster | 0.12 |
| (13) deionized water | balance |

Method of Production

Ingredients (1) to (13) were heated at 70° C. with stirring to prepare a homogeneous mixture. Subsequently, the mixture was cooled, to thereby obtain a conditioning shampoo.

Comparative Example 1
Hair Blow (Keratose-free)

| Ingredient | Amount (wt. %) |
|---|---|
| (1) decamethylcyclopentasiloxane | 15.0 |
| (2) dimethylpolysiloxane (20 mPa · s) | 3.0 |
| (3) 1,3-butylene glycol | 2.0 |
| (4) polyoxyethylene hydrogenated castor oil (60EO) | 2.0 |
| (5) hydrolyzed keratin [Promois WK-H, product of Seiwa Kasei Co., Ltd.] | 1.0 |
| (6) ethanol | 15.0 |
| (7) deionized water | balance |
| (8) perfume | 0.3 |

Ingredient (2) was added to Ingredient (1), and the mixture was added to a mixture of Ingredients (3) and (4). The resultant mixture was emulsified. Subsequently, the emulsion was mixed with Ingredients (5) to (8), to thereby obtain a hair blow.

Comparative Example 2
Hair Mousse (Silicone Derivative-free)

| Ingredient | Amount (wt. %) |
|---|---|
| (1) isocetyl isostearate | 10.0 |
| (2) liquid paraffin | 2.0 |
| (3) propylene glycol | 2.5 |
| (4) polyoxyethylene hydrogenated castor oil (40EO) | 2.0 |
| (5) α-keratose (Production Ex. 1) | 2.5 |
| (6) γ-keratose (Production Ex. 2) | 2.5 |
| (7) ethanol | 8.0 |
| (8) deionized water | balance |
| (9) n-butane | 7.0 |
| (10) perfume | 0.1 |

Method of Production

Ingredient (2) was dissolved in Ingredient (1), and the mixture was added to a mixture of Ingredients (3) and (4). The resultant mixture was emulsified. Subsequently, the emulsion was mixed with Ingredients (5), (6), (7), (8), and (10), to thereby prepare a solution, which was charged into an aerosol container. The container was equipped with a stopper valve, and filled with Ingredient (9), to thereby obtain a hair mousse.

Comparative Example 3
Hair Cream (Keratose-free)

| Ingredient | Amount (wt. %) |
|---|---|
| (1) decamethylcyclohexasiloxane | 25.0 |
| (2) amino-modified high-molecular-weight silicone [formula (II), wherein R$^6$ represents a methyl group, R$^7$ represents a hydroxyl group; R$^8$ represents -(CH$_2$)$_3$N(CH$_3$)$_2$; x is 3000; and y is 6] | 6.0 |
| (3) glycerin | 3.0 |
| (4) polyoxyethylene hydrogenated castor oil (120EO) | 3.0 |
| (5) cationized and hydrolyzed collagen [Promois W-52QP, product of Seiwa Kasei Co., Ltd.] | 1.0 |
| (6) ethanol | 10.0 |
| (7) deionized water | balance |

-continued

| Ingredient | Amount (wt. %) |
|---|---|
| (8) polyvinyl alcohol | 1.0 |
| (9) perfume | 0.1 |

Method of Production

Ingredient (2) was dissolved in Ingredient (1), and thqe mixture was added to a mixture of Ingredients (3) and (4). The resultant mixture was emulsified. Subsequently, the emulsion was mixed with Ingredients (5) to (9), to thereby obtain a hair cream.

Comparative Example 4
Hair Gel (Silicon Derivative-free, Keratose-free)

| Ingredient | Amount (wt. %) |
|---|---|
| (1) polyoxyethylene (4.5EO) polyoxypropylene (65PO) pentaerythritol ether | 3.0 |
| (2) carboxyvinylpolymer [Hiviswako 104, product of Wako Pure Chemicals Industries, Ltd.] | 2.0 |
| (3) glycerin | 5.0 |
| (4) vinylpyrrolidone/vinyl acetate copolymer (PVP/VA · S-630, product of ISP] | 3.0 |
| (5) soybean lecithin | 5.0 |
| (6) ethanol | 5.0 |
| (7) deionized water | balance |
| (8) sodium hydroxide | 0.5 |
| (9) perfume | 0.5 |

Method of Production

Ingredient (2) was dissolved in Ingredient (7). To the mixture, Ingredients (1), (3), (4), (5), (6), (8), and (9) were successively added, to thereby obtain a hair gel.

Comparative Example 5
Conditioning Shampoo (Keratose-free)

| Ingredient | Amount (wt. %) |
|---|---|
| (1) triethanolamine lauryl polyoxyethylene (3) sulfate (30% aq. solution) | 10.0 |
| (2) sodium lauryl polyoxyethylene (3) sulfate (30% aq. solution) | 20.0 |
| (3) sodium lauryl sulfate (30% aq. solution) | 5.0 |
| (4) lauroyldiethanolamide | 3.0 |
| (5) lauryl dimethylaminoacetic acid betaine (35% aq. solution) | 7.0 |
| (6) dimethylsilicone emulsion | 2.5 |
| (7) ethylene glycol disearate | 2.0 |
| (8) perfume | 0.3 |
| (9) paraben | 0.1 |
| (10) sequestering agent | 0.1 |
| (11) pH-adjuster | 0.12 |
| (12) deionized water | balance |

Method of Production

Ingredients (1) to (12) were heated at 70° C. with stirring to prepare a homogeneous mixture. Subsequently, the mixture was cooled, to thereby obtain a conditioning shampoo.

Methods for Testing Samples (1) Stickiness to the Hands

Each sample (1 g) was put on the palm, and scrubbed with both hands for 30 seconds. Stickiness to the hands was sensorially evaluated on the basis of the following standards:

BB: free of stickiness

CC: slightly sticky

DD: very sticky.

(2) Ease of Combing

Each sample (2 g) was applied to damaged hair strands (4 g). After application of the samples, the hair strands were shaped by means of a comb. Ease of combing was sensorially evaluated on the basis of the following standards, immediately after application and six hours after application:

AA: very smooth combing

BB: smooth combing

CC: combing with little resistance

DD: combing with much resistance.

(3) Smoothness

In a manner similar to that of the aforementioned test (2), smoothness of damaged hair was sensorially evaluated on the basis of the following standards, immediately after application and six hours after application:

AA: very smooth

BB: smooth

CC: fairly smooth

DD: not smooth.

(4) Gloss of Hair

Each sample (1 g) was applied to a bundle of 500–600 damaged hairs having a length of 15 cm. The bundle was subjected to shake-rinsing (100 cycles) twice in warm water (300 ml) at 40° C., and dried. Ten arbitrary hairs were picked from the bundle and subjected to measurement of reflected light distribution to light incident to the hairs. The measurement was carried out by means of a deformation photometer GP-IR (product of Murakami Sikisai Kenkyu-sho), and glossiness of hair was obtained on the basis of the following formula:

$$G \text{ (glossiness)} = s \text{ (regular reflection)}/d \text{ (diffusion reflection)}.$$

The effect of each sample in imparting gloss to hair was evaluated through the thus-obtained glossiness (G) on the basis of the following standards:

| G | | Evaluation (effect in imparting gloss) |
|---|---|---|
| higher than 15 | AA | excellent |
| 10–15 | BB | moderate |
| 5–10 | CC | little |
| lower than 5 | DD | none |

Gloss of damaged hair strands was sensorially evaluated immediately after application and six hours after application, as in the aforementioned tests (2) and (3).

(5) Effect in Mending Split Ends

Hairs (30 cm/5 g) obtained from Japanese women, which had split ends, were bundled, and each bundle was shampooed. Each sample (approximately 5 g) was directly applied to one of the bundles, and the bundle was lightly rinsed off. Subsequently, the bundle was brushed to dryness by use of a brush and a hair-dryer. Re-splitting of mended hairs was evaluated on the basis of the following standards, after completion of another ten brushings:

AA: no re-splitting occurred

BB: mended ends slightly split

CC: mended ends almost split
DD: not mended at all

TABLE 2

|  |  | (1) Stickiness | (2) Ease of combing | (3) Smoothness | (4) Hair gloss | (5) Mending of split ends |
|---|---|---|---|---|---|---|
| Example 1 | 0* | BB | AA | AA | BB | BB |
|  | 6** | — | BB | BB | BB | — |
| Example 2 | 0* | BB | AA | AA | AA | AA |
|  | 6** | — | AA | AA | AA | — |
| Example 3 | 0* | BB | AA | AA | AA | AA |
|  | 6** | — | AA | AA | AA | — |
| Example 4 | 0* | BB | AA | AA | AA | AA |
|  | 6** | — | AA | AA | BB | — |
| Comp. Ex. 1 | 0* | CC | BB | BB | BB | BB |
|  | 6** | — | CC | BB | CC | — |
| Comp. Ex. 2 | 0* | BB | CC | BB | CC | CC |
|  | 6** | — | CC | CC | CC | — |
| Comp. Ex. 3 | 0* | CC | CC | CC | BB | BB |
|  | 6** | — | CC | DD | BB | — |
| Comp. Ex. 4 | 0* | DD | CC | CC | BB | DD |
|  | 6** | — | DD | DD | CC | — |

*0; immediately after application
**6; 6 hours after application

As is clear from Table 2, the hair cosmetic composition of the present invention imparts excellent gloss and smoothness to hair. In addition, the composition bonds split ends of hair fibers, to thereby successfully mend split ends.

What is claimed is:

1. A hair-cosmetic composition comprising the following ingredients (A) and (B):
   (A): keratose which is cationized with a quaternary ammonium salt, and
   (B): a silicone derivative.

2. The composition according to claim 1, wherein the keratose is at least one selected from the group consisting of α-keratose and γ-keratose.

3. The composition according to claim 1, wherein the quaternary ammonium salt is represented by the following formula (1):

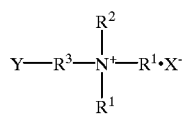

(1)

wherein each of two $R^1$, which may be the same or different from each other, represents a lower alkyl group; $R^2$ represents a $C_1$–$C_{20}$ alkyl group or a $C_2$–$C_{20}$ alkenyl group; $R^3$ represents a $C_1$–$C_{24}$ alkylene group or a hydroxyalkylene group; X represents a halogen atom; Y represents a reactive group; and $R^3$ and Y may be linked to each other to form a glycidyl group.

4. The composition according to claim 1, wherein the silicone derivative is at least one selected from the group consisting of high-molecular-weight silicone represented by formula (I):

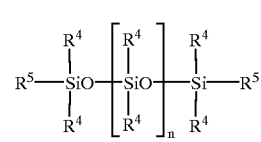

(I)

wherein $R^4$ represents a methyl group or a phenyl group (not all $R^4$ represents a phenyl group), $R^5$ represents a methyl group or a hydroxyl group, and n represents an integer of 3,000–20,000; and.

amino-modified or ammonium-modified high-molecular-weight silicone which is a silicone derivative represented by formula (II):

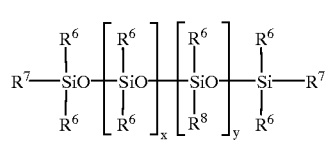

(II)

wherein $R^6$ represents a methyl group or a phenyl group (not all $R^6$ represents a phenyl group), $R^7$ represents a methyl group, a hydroxyl group, or the same group as $R^8$, $R^8$ represents a substituent having an amino group or an ammonium group, which substituent is represented by formula $R^9Z$ ($R^9$ represents a $C_3$–$C_6$ alkylene group and Z represents a monovalent group selected from the group consisting of —N($R^{10}$)$_2$, —N$^+$($R^{10}$)$_3$A$^-$, —N($R^{10}$)(CH$_2$)$_d$N($R^{10}$)$_2$, —NR$^{10}$(CH$_2$)$_d$N$^+$($R^{10}$)$_3$A$^-$, and —NR$^{10}$(CH$_2$)$_d$N($R^{10}$))C=O($R^{11}$), wherein $R^{10}$ represents a hydrogen atom or a $C_1$–$C_4$ alkyl group, $R^{11}$ represents a $C_1$–$C_4$ alkyl group, A represents chlorine, bromine, or iodine, and d represents an integer of 2–6), and each of x and y represents a positive integer, x+y being 3,000–20,000 and y/x being 1/500–1/10,000.

5. The composition according to claim 1, wherein the keratose is contained in an amount of 0.01–5.0 wt. % and the silicone derivative is contained in an amount of 1.0–30.0 wt. % on the basis of the entirety of the composition.

6. The composition according to claim 4, wherein both of the high-molecular-weight silicone (I) and the amino-modified or ammonium-modified high-molecular-weight silicone (II) are contained.

7. The composition according to claim 6, wherein the weight ratio of the high-molecular-weight silicone (I) and the amino-modified or ammonium-modified high-molecular-weight silicone (II) is 1:9–9:1.

* * * * *